United States Patent [19]
Martini et al.

[11] Patent Number: 5,126,333
[45] Date of Patent: Jun. 30, 1992

[54] PHARMACEUTICAL COMPOSITIONS HAVING IMPROVED DISSOLUTION PROPERTIES

[75] Inventors: Alessandro Martini; Clara Torricelli; Carlo Confalonieri; Roberto De Ponti, all of Milan, Italy

[73] Assignee: Farmitalia Carlo Erba S.R.L., Milan, Italy

[21] Appl. No.: 561,577

[22] Filed: Aug. 2, 1990

[30] Foreign Application Priority Data

Sep. 6, 1989 [GB] United Kingdom ............... 8920135

[51] Int. Cl.⁵ ................. A61K 31/70; C08B 37/16
[52] U.S. Cl. ................................ 514/58; 536/103; 514/778
[58] Field of Search ............... 536/103; 514/58, 778

[56] References Cited

U.S. PATENT DOCUMENTS 4,726,064  2/1988  Pitha .................................. 514/58

FOREIGN PATENT DOCUMENTS 56-61369   5/1981  Japan .
61-21184   1/1986  Japan .
62-267261 11/1987  Japan .
63-135402  6/1988  Japan .
1357410   12/1987  U.S.S.R. .

Primary Examiner—Ronald W. Griffin
Attorney, Agent, or Firm—Oblon, Spivak, McClelland, Maier & Neustadt

[57] ABSTRACT

A pharmaceutical composition comprising a drug and a dehydrated cyclodextrin having improved dissolution properties, and the process for the preparation thereof.

9 Claims, No Drawings

PHARMACEUTICAL COMPOSITIONS HAVING IMPROVED DISSOLUTION PROPERTIES

The present invention relates to pharmaceutical compositions comprising at least an active drug substance together with a dehydrated cyclodextrin as drug dissolution improving agent, and to a process for the preparation thereof.

The improvement of the drug dissolution is one of the most common problems in the pharmaceutical field, and cyclodextrins often provide to be an effective means to obviate such a problem.

Cyclodextrins (hereinafter CD) are well known compounds having a cylindrical cavity shaped structure capable of including various guest molecules. Indeed, one of the most interesting properties of CD is their ability to form inclusion compounds or complexes. At the pharmaceutical level, the applications of these inclusions are essentially for improving the stability and, above all, solubility, dissolution characteristics and the bioavailability of the included molecule. Said inclusions are usually prepared in a liquid medium, e.g. in the presence of water or other solvents, and then, upon drying, they are obtained in powder form. Techniques commonly used are: the co-precipitation method (Crassons et al., 5th Int. Conf. on Pharmaceutical Technology, Paris, 30 May-1st Jun. 1989); the freeze-drying or spray-drying method [Koruzu-mi et al., Chem. Pharm. Bull. 23, 3062 (1975); Kata et al., Pharmazie 39, 856 (1984)]; the phase-solubility diagram crystallization [Uekama et al., Int. J. Pharmac. 10, 1 (1982)]; or the kneading method [J. Szejtli, "Cyclodextrins and their inclusion complexes", Akadeimiai Kiado, Budapest (1982), p. 109-114; Kyowa Jap.Prov.Pat.Publn. No. 106698 (1982)]. In some cases the formation of the complex in the solid phase is thermodinamically spontaneous and inclusion is normally achieved by grinding [Terada et al., 3rd Int. Conf. on Pharmaceutical Technology, Paris, 31 May, 2 Jun. 1983, Vol. V, 246; Carli et al., Chimica oggi, 61, May 1987; S. Y. Lin et al., Drug Dev.Ind.Pharm., 14(1), 99-118 (1988)] or rolling [Nozawa and Yamamoto, Pharm. Acta Helv., 64 (1), 24 (1984)].

The CD employed in the preparation of the complex is generally used either as such or recrystallized from water, and its water content is of about 12-14%. A drying process is normally applied to the just formed inclusion compound or complex in order to eliminate solvent and adjust the moisture content to the desired percentage. In fact various molecules of water may be complexed with one CD molecule. A. Szafraneck (J. Therm. Analysis, vol. 34, 917-925, 1988) reports that said molecules of water are shared between the cavity of cyclodextrin and the external interstices. The formation of drug-CD complexes involves the removal of the included water molecules because the drug completely or partially substitutes them in the cavity of CD.

We have now found that the dissolution characteristics and bioavailability of drugs can be still more improved through the use of anhydrate or dehydrate CD, i.e. CD wherein the included water has been almost completely eliminated before combining the CD with the drug.

Accordingly, the present invention provides a pharmaceutical composition comprising at least an active drug substance and an anhydrate or dehydrated CD.

Though the invention generally refers to the use of any CD in dehydrated form, it is particularly directed to the use of those CD which retain water of crystallization, especially $\beta$-CD. The term "anhydrated or dehydrated CD" means a CD which has a water content lower than 5% by weight. Clearly, such definition includes also a CD which has the 0% of water content, that is an anhydrate CD.

Typically the residual moisture content of the drug-CD composition according to the present invention is lower than 9%, preferably lower than 5% by weight. Possibly the moisture content can be also lower than 2% by weight. Such very low residual moisture content may therefore be obtained by using anhydrate or dehydrated CD according to the invention.

The proportion between the drug substance and the dehydrated CD may vary, e.g., from 1:0.5 to 1:10 (molar ratio). A preferred molar ratio is from 1:1 to 1:4. Suitable ranges can be of 1:1 and 1:2.

According to the invention the drug-CD composition is prepared by a process which comprises mixing a solid active drug substance and a solid dehydrated CD having the above said water content. This may be achieved by simple mechanical mixing or by co-grinding technique, to give a drug-CD composition of very low water content, which, when brought into solution may lead to a true drug-CD inclusion compound.

By "co-grinding" is meant that a solid drug and a solid dehydrated CD are first simply mixed together and then ground together. Such technique, which may be defined as a "mechano-chemical activation", gives better results than other preparation processes due, partially, to complex formation and/or amorphization of the drug molecularly dispersed in the carrier and, partially, to the increase of the surface area developed.

Therefore, in one embodiment, the solid drug substance and the solid dehydrated CD are mixed together under controlled relative humidity conditions so that the resulting mixture has a residual moisture content lower than 5% by weight.

In another embodiment, the solid drug substance and the solid dehydrated CD are mixed together and then further mixed by grinding under controlled relative humidity conditions so that the resulting mixture has a residual moisture content lower than 9% by weight. For the co-ground compositions a somewhat higher moisture content may be accepted in view of the fact that the moisture absorption can be hardly avoided during grinding operations.

When a co-grinding procedure is employed, the grinding parameters such as, e.g., time, powder-grinding media, volume to volume ratio and so on, should be carefully selected depending on the molar ratio between the two components.

For the preparation of the drug-CD compositions of the invention, the dehydrated CD may be used either as such or after pre-milling in order to adjust the particle size to the desired diameter range. Of course in this case materials need to be manipulated under controlled relative humidity conditions to avoid re-hydration.

To obtain the dehydrated CD useful for invention, a commercially available CD, that is a hydrated form containing, e.g., 12% to 14% by weight of water, is typically heated in an oven at a temperature which, depending on the heating time, may vary from about 100° to about 220° C., preferably from about 100° to about 140° C. The heating may be continued from about 2 up to about 48 hours, depending on the temperature, preferably for 8 to 12 hours, either at ambient pressure or under vacuum, in the presence or absence of an inert gas (stationary or flow through), preferably in the presence of a non-interacting dessicant agent, e.g. silica gel, calcium chloride, phosphorous pentoxide, preferably silica gel. Particularly preferred conditions involve the use of mechanical vacuum and a temperature ranging from about 115° C. to about 130° C. for 8 hours.

Any active drug substance, especially any substance having solubility problems and capable or interacting with CD, may be advantageously employed to give a drug-CD composition according to the invention, either as physical mixture or as co-ground composition.

Examples of drug substances may be steroids, for instance medroxyprogesterone acetate (MPA), progesterone, testosterone, prednisolone, dexamethasone, betamethasone, 6-methyleneandrosta-1,4-diene-3,17-dione and the like; antibiotics such as e.g., griseofulvin, cefalosporins, penicillins, penems and the like; antidepressant drugs such as, e.g., benzodiazepins, e.g. temazepam, oxazepam, diazepam, nitrazepam and the like; immunomodulators such as, e.g., 2-cyano-3-(1,4-dihydro-1-phenyl-(1)-benzothiopyran)-(4,3-C)-pyrazol-3-yl-3-oxo-N-phenylpropanamide and the like; antiinflammatory agents such as, e.g., indomethacin, indoprofen, ketoprofen, flufenamic acid and the like; antineoplastic agents such as, e.g. anthracycline glycosides, e.g. idarubicin (i.e. 4-demethoxy daunorubicin), doxorubicin, 3'-deamine-3'-(3-cyano-4-morpholinyl)-doxorubicin and the like, etoposide, teniposide and other podophyllotoxins.

The drug-CD physical or co-ground mixtures according to the invention can be used to prepared solid, especially oral, dosage forms, e.g. capsules, tablets, sachets and so on, with or without the addition of one or more of the excipients commonly used in pharmaceutical formulation.

A pharmaceutical formulation containing the drug-CD composition of the invention, which is included within the scope of the invention, can be prepared following known and conventional procedures. A pharmaceutically acceptable carrier or diluent may be present.

The drug-CD composition obtained as indicated above surprisingly show a remarkably improved dissolution behaviour of the active substance. The Tables of this specification report a comparison between the dissolution behaviour of a drug inserted in a physical mixture according to the invention, i.e. a physical mixture of the active substance with dehydrated CD, and a corresponding physical mixture obtained according to a prior art technique, i.e. using hydrated CD.

A comparison of the dissolution profiles shows how the concentration of the drug released in the solution is remarkably and unexpectedly greater with the drug-dehydrated CD compositions according to the invention. The improvement is especially and surprisingly evident in those cases where the drug is pratically insoluble.

It is well known that the increase in drug solubility is produced by inclusion complex formation in solution, and a drug-CD complex in solution is always in kinetic and thermodynamic equilibrium with its free components. Generally this equilibrium is quantitatively described by stability constants which are parameters indicating the affinity between the active substance and the complexing agent, i.e. CD. A general method used for the detection of stability constants is based in monitoring changes in solubility of the drug by adding CD at constant temperature.

Surprisingly it has been observed that, using dehydrated CD the same enhancement in drug solubility obtained by using hydrated ones could be reached, but in a shorter time, as it can be seen in a short time solubility kinetic test shown hereinafter.

Furthermore it has been observed that the increased and more rapid dissolution of the drug achieved with the pharmaceutical compositions according to the invention may be accompanied, at the solid state, by any change in surface area or wettability of the powder.

The contact surface area between the solid substance and the liquid medium is an important parameter influencing the dissolution rate, i.e. the greater the area the easier the dissolution. It has been surprisingly found that by using dehydrated CD the improvement in the dissolution rate is not due to differences in surface area, i.e. a composition comprising a dehydrated CD having the same surface area of a hydrated one provides a faster and better dissolution behaviour. In fact, the dissolution of mixtures simply prepared by physically mixing both the components, was investigated using the rotating disk method for the determination of the intrinsic dissolution rate of the compositions |(Corrigan O. I. et al., Int.J.Pharm., 4, 67 (1969)|. The intrinsic dissolution rate is higher for compositions containing dehydrated CD than hydrated ones.

The following Examples are only given with the purpose of better illustrating the invention but in no way they must be considered as a limitation of the scope of the invention itself. All the dissolution behaviour tests were made using USP XXII No. 2 dissolution test (paddle method) in sink conditions. The FCE numerical codes or internal codes used to identify compounds whose chemical name is given in the Examples after the code itself. Percentages are by weight.

EXAMPLE 1

10 g of β-cyclodextrin (containing about 12% of water) were put in an oven under light vacuum (30 mmHg) at 130° C. for 8 hours in presence of, as a non-interacting dessicant, silica gel. After cooling, the β-cyclodextrin recovered (8.96 g) was checked by Karl Fisher analysis (water content 1.75%), elemental analysis, differential scanning calorimetry, thermogravimetric analysis and X-ray diffraction pattern.

EXAMPLE 2

Operating under controlled moisture conditions 2 g of FCE 24578 /(2-cyano-3-(1,4-dihydro-1-phenyl-(1)-benzothiopyran)-(4,3-C)-pyrazol-3-yl)-3-oxo-N-phenyl-propanamide)| (0.0044 mol) and 5 g of dehydrated β-cyclodextrin from Example 1 (0.0044 mol) were sieved together through a 115 m sieve and then mixed with a tumbler for 30 min. An equimolar drug/hydrated β-cyclodextrin (12.15% of water in it) physical mixture was prepared as comparison. Dissolution behaviour tests were carried out to compare each mixture. The conditions of the test were phosphate buffer pH 7.4, 37° C. and 120 rpm. The results are shown in Table 1.

TABLE 1

| FCE 24578/β-cyclodextrin physical mixtures | | |
|---|---|---|
| time | (percent in solution) | |
| (minutes) | hydrated β-CD | dehydrated β-CD |
| 0 | 0.0 | 0.0 |
| 15 | 1.0 | 10.5 |

TABLE 1-continued

| | FCE 24578/β-cyclodextrin physical mixtures | |
|---|---|---|
| time | (percent in solution) | |
| (minutes) | hydrated β-CD | dehydrated β-CD |
| 30 | 2.4 | 10.8 |
| 45 | 3.7 | 10.1 |
| 60 | 5.3 | 10.6 |

EXAMPLE 3

Operating under controlled moisture conditions 2.49 g of FCE 24304 |6-methyleneandrosta-1,4-diene-3,17-dione| (0.0084 mol) and 9.52 g of dehydrated β-cyclodextrin from Example 1 (0.0084 mol) were sieved together through a 115 m sieve and then mixed with a tumbler for 15 min. An equimolar drug/hydrated β-cyclodextrin physical mixture was prepared as comparison. Dissolution behaviour tests were carried out to compare each mixture. The conditions of the test were phosphate buffer pH 7.4, 37° C. and 150 rpm. The results are shown in Table 2.

TABLE 2

| | FCE 24304/β-cyclodextrin physical mixtures | |
|---|---|---|
| time | (percent in solution) | |
| (minutes) | hydrated β-CD | dehydrated β-CD |
| 0 | 0.0 | 0.0 |
| 1 | 3.7 | 6.7 |
| 3 | 8.4 | 16.0 |
| 5 | 12.9 | 23.2 |
| 10 | 20.8 | 34.2 |
| 15 | 27.9 | 41.8 |
| 30 | 40.7 | 52.4 |
| 60 | 54.4 | 62.5 |

The same improvements were obtained using a 1:2 mol/mol ratio drug/dehydrated β-cyclodextrin physical mixture versus an analogous hydrated one.

EXAMPLE 4

The same procedure as for Example 3 was used using medroxypregesterone (17 -acetoxy-6 -methyl-pregn-4-ene-3,20-dione) as drug in a molar ratio 1:1 with β-cyclodextrin. Dissolution behaviour tests were carried out to compare each mixture. The conditions of the tests were water plus 0.05% by weight sodium laurylsulfate, 37° C. and 100 rpm. The results are shown in Table 3.

TABLE 3

| | Medroxyprogesterone acetate/β-cyclodextrin physical mixtures | |
|---|---|---|
| time | (percent in solution) | |
| (minutes) | hydrated β-CD | dehydrated β-CD |
| 0 | 0.0 | 0.0 |
| 1 | 3.19 | 3.04 |
| 3 | 8.40 | 9.27 |
| 5 | 14.76 | 15.78 |
| 10 | 28.91 | 32.19 |
| 15 | 41.56 | 45.29 |
| 30 | 63.42 | 67.79 |
| 60 | 76.24 | 81.92 |
| 90 | 86.10 | 88.28 |
| 120 | 86.72 | 91.32 |

The same improvements were obtained using a 1:2 mol/mol ratio drug/dehydrated β-cyclodextrin physical mixture versus analogous hydrated one.

EXAMPLE 5

The same procedure as for Example 3 was used using temazepam (7-chloro-1,3-dihydro-3-hydroxy-1-methyl-5-phenyl-2H-1,4-benzo-diazepine-2-one) as drug in a molar ratio 1:1 with β-cyclodextrin.

Dissolution behaviour tests were carried out to compare each mixture. The conditions of the test were phosphate buffer pH 7.4, 37° C. and 100 rpm. The results are shown in Table 4.

TABLE 4

| | Temazepam/β-cyclodextrin physical mixtures | |
|---|---|---|
| time | (percent in solution) | |
| (minutes) | hydrated β-CD | dehydrated β-CD |
| 0 | 0.0 | 0.0 |
| 5 | 11.3 | 22.7 |
| 10 | 23.0 | 33.9 |
| 15 | 35.0 | 45.8 |
| 20 | 46.1 | 57.7 |
| 30 | 58.9 | 74.2 |
| 45 | 72.3 | 86.8 |
| 60 | 79.4 | 91.8 |

EXAMPLE 6

Operating under controlled moisture conditions 2 g of FCE 24578 (0.0044 mol) and 5 g of dehydrated β-cyclodextrin from Example 1 (0.0044 mol) previously premixed with a tumbler were placed in a high energy mill and ground for 2 hours. The resulting ground composition was sieved through a 115 m sieve and then mixed with a tumbler. Two different 1:1 drug/hydrated β-cyclodextrin co-ground compositions were made as comparison in the same operative conditions: the first one using hydrated β-cyclodextrin as is, the other one using hydrated β-cyclodextrin just pre-ground for 2 hours.

Dissolution behaviour tests were carried out to compare each mixture. The conditions of the test were phosphate buffer pH 7.4, 37° C. and 120 rpm. The results are shown in Table 5.

TABLE 5

| | FCE 24578/β-cyclodextrin co-ground compositions | | |
|---|---|---|---|
| | (percent in solution) | | |
| time (minutes) | hydrated β-CD as is | hydrated β-CD preground | dehydrated β-CD |
| 0 | 0.0 | 0.0 | 0.0 |
| 15 | 69.8 | 79.1 | 91.6 |
| 30 | 79.3 | 82.9 | 90.9 |
| 45 | 80.4 | 83.4 | 91.6 |
| 60 | 82.3 | 82.3 | 90.3 |

EXAMPLE 7

Operating under controlled moisture conditions 2.5 g of Griseofulvin (7-chloro-2',4,6-trimethoxy-6'-methyl-spiro|-benzofuran-2(3H)-1'|2|cyclohexene|-3,4'-dione) (0.0070 mol) and 7.5 g of dehydrated β-cyclodextrin from Example 1 (0.0066 mol) previously premixed were ground for 1 hour in a high energy mill. The resulting ground composition was sieved through a 115 m sieve and then mixed with a tumbler.

Dissolution behaviour tests of this mixture was compared with an analogous co-ground composition with hydrated β-cyclodextrin.

The conditions of the tests were phosphate buffer pH 7.4, 37° C. and 80 rpm. The results are shown in Table 6.

TABLE 6

| Griseofulvin/β-cyclodextrin co-ground compositions | | |
|---|---|---|
| time | (percent in solution) | |
| (minutes) | hydrated β-CD | dehydrated β-CD |
| 0 | 0.0 | 0.0 |
| 5 | 25.3 | 40.4 |
| 10 | 35.4 | 52.7 |
| 15 | 44.0 | 58.3 |
| 20 | 50.9 | 61.4 |
| 30 | 55.5 | 65.3 |
| 45 | 60.6 | 68.0 |
| 60 | 64.6 | 71.3 |
| 90 | 68.3 | 73.7 |
| 120 | 71.2 | 75.0 |

EXAMPLE 8

Operating under controlled moisture conditions 2.49 g of FCE 24304 (0.0084 mol) and 9.54 g of dehydrated β-cyclodextrin from Example 1 (0.0084 mol) previously premixed with a tumbler, were placed in a high energy mill and ground for 2 hours. The resulting ground composition was sieved through a 115 m sieve and subsequently mixed with a tumbler. Dissolution behaviour tests of this mixture was compared with an analogous co-ground composition with hydrated β-cyclodextrin. The conditions of the tests were phosphate buffer pH 7.4, 37° C. and 150 rpm. The results are shown in Table 7.

TABLE 7

| FCE 24304/β-cyclodextrin co-ground compositions | | |
|---|---|---|
| time | (percent in solution) | |
| (minutes) | hydrated β-CD | dehydrated β-CD |
| 0 | 0.0 | 0.0 |
| 1 | 47.0 | 56.7 |
| 3 | 69.0 | 78.3 |
| 5 | 77.3 | 84.2 |
| 10 | 84.2 | 89.6 |
| 15 | 86.3 | 91.0 |
| 30 | 89.5 | 93.9 |
| 60 | 91.7 | 95.9 |

The same improvements were obtained using a 1:2 mol/mol ratio between drug and dehydrated β-cyclodextrin co-ground composition versus an analogous one with hydrated B-cyclodextrin.

EXAMPLE 9

250 mg of an equimolecular FCE 24304/dehydrated β-cyclodextrin physical mixture prepared according to Example 3 were compressed to obtain a no-disgregating disk (surface area of 1.02 cm$^{-2}$). A disk of equimolecolar drg/hydrated β-cyclodextrin physical mixture was prepared with the same force of compression as comparison.

The conditions of the tests were phosphate buffer, pH 7.4, 37° C. and 100 rpm. The results are shown in Table 8.

TABLE 8

| FCE 24304/β-cyclodextrin physical mixtures | | |
|---|---|---|
| time | (mcg/ml) | |
| (minutes) | hydrated β-CD | dehydrated β-CD |
| 0 | 0.0 | 0.0 |
| 2 | 0.49 | 0.69 |
| 4 | 0.72 | 1.12 |
| 6 | 1.06 | 1.52 |
| 8 | 1.32 | 1.94 |
| 10 | 1.71 | 2.24 |
| 12 | 1.97 | 2.64 |
| 14 | 2.29 | 3.06 |
| 16 | 2.63 | 3.53 |
| 18 | 2.86 | 4.00 |
| 20 | 3.20 | 4.46 |

EXAMPLE 10

250 mg of en equimolecular temazepam/dehydrated β-CD physical mixture prepared according to Example 5, was compressed obtaining a non disgregating disk. Disk of equimolecular drug/hydrated β-CD physical mixture was prepared with the same force of compression as comparison.

The conditions of the tests were phosphate buffer, pH 7.4, 37° C. and 100 rpm. Results are shown in Table 9.

TABLE 9

| FCE Temazepam/β-cyclodextrin physical mixtures | | |
|---|---|---|
| time | (mcg/ml) | |
| (minutes) | hydrated β-CD | dehydrated β-CD |
| 0 | 0.0 | 0.0 |
| 2 | 0.47 | 1.35 |
| 4 | 0.86 | 2.35 |
| 6 | 1.31 | 3.10 |
| 8 | 1.70 | 3.72 |
| 10 | 2.17 | 4.33 |
| 12 | 2.58 | 4.91 |
| 14 | 3.06 | 5.46 |
| 16 | 3.42 | 6.08 |
| 18 | 3.84 | 6.48 |
| 20 | 4.24 | 7.03 |

EXAMPLE 11

A dehydrated β-CD powder bed (about 200 mg) is packed and put in a liquid penetrometer apparatus for penetrated volume measurements according to Nogami et al. Chem.Pharm.Bull. 17, 1450 (1969). The penetrating volume of distilled water was detected as function of time and penetration rate constant calculated. Hydrated β-CD penetration measurements were detected as comparison. Penetrated volumes per weight unit and constants are shown in Table 10.

TABLE 10

| Time | penetrated volumes (ml/g) | |
|---|---|---|
| (seconds) | Hydrated β-CD | Dehydrated β-CD |
| 15 | 0.031 | 0.035 |
| 30 | 0.049 | 0.055 |
| 45 | 0.060 | 0.087 |
| 60 | 0.070 | 0.122 |
| 75 | 0.084 | 0.157 |
| 90 | 0.097 | 0.192 |
| 105 | 0.106 | 0.227 |
| 120 | 0.116 | 0.261 |
| 135 | 0.128 | 0.294 |
| 150 | 0.137 | 0.328 |
| 165 | 0.147 | 0.361 |
| 180 | 0.154 | 0.388 |
| 210 | 0.171 | 0.448 |
| 240 | 0.190 | 0.503 |
| 270 | 0.210 | 0.560 |
| 300 | 0.229 | 0.612 |
| 360 | 0.265 | 0.714 |
| 420 | 0.299 | 0.811 |
| 480 | 0.340 | 0.903 |
| Penetration rate constants | | |
| hydrated cyclodextrin | K = 3.9 × 10$^{-4}$ ml/g sec | |

TABLE 10-continued

| Time | penetrated volumes (ml/g) | |
|---|---|---|
| (seconds) | Hydrated β-CD | Dehydrated β-CD |
| dehydrated cyclodextrin | $K = 2.0 \times 10^{-3}$ ml/g sec | |

EXAMPLE 12

The water penetration rate of temazepam/β-CD 1:1 mol/mol (both hydrated and dehydrated) mixture, obtained by physical mixing, are measured as described in Example 11. Penetrated volumes and constants are shown in Table 11.

TABLE 11

| | Temazepam/β-CD physical mixtures | |
|---|---|---|
| Time | penetrated volumes (ml/g) | |
| (seconds) | Hydrated β-CD | Dehydrated β-CD |
| 15 | 0.056 | 0.068 |
| 30 | 0.071 | 0.110 |
| 45 | 0.089 | 0.155 |
| 60 | 0.105 | 0.199 |
| 90 | 0.136 | 0.290 |
| 120 | 0.165 | 0.364 |
| 150 | 0.192 | 0.432 |
| 180 | 0.216 | 0.497 |
| 210 | 0.241 | 0.557 |
| 240 | 0.261 | 0.618 |
| 270 | 0.281 | 0.671 |
| 300 | 0.301 | 0.717 |
| 330 | 0.318 | 0.766 |
| 360 | 0.339 | 0.806 |
| Penetration rate constants | | |
| hydrated β-CD | $K = 4.4 \times 10^{-4}$ ml/g sec | |
| dehydrated β-CD | $K = 2.2 \times 10^{-3}$ ml/g sec | |

EXAMPLE 13

Accurately weighted amounts of temazepam (750 mg) were added to flasks containing acetate buffer, pH 5.5 (50 ml) in which increasing amounts of dehydrated β-CD were dissolved. The capped flasks were shaken (120 rpm) at 37° C. The active substance concentration was detected by HPLC on the previously filtered samples after 15 minutes and after 4 hours. An analogous experiment was carried out using hydrated instead of dehydrated β-CD. Experimental data are shown in Table 12.

TABLE 12

| Solubility of temazepam with different concentrations of β-CD hydrated and dehydrated | | | | |
|---|---|---|---|---|
| | Drug in solution concentration | | | |
| | 15 minutes | | 4 hours | |
| | (mg/ml) | (mmol/l) | (mg/ml) | (mmol/l) |
| Hydrated cyclodextrin (mmol/l) | | | | |
| 0.25 | 0.131 | 0.435 | 0.145 | 0.482 |
| 1.00 | 0.133 | 0.442 | 0.159 | 0.529 |
| 5.00 | 0.177 | 0.588 | 0.221 | 0.735 |
| 10.00 | 0.249 | 0.828 | 0.312 | 1.037 |
| 20.00 | 0.286 | 0.951 | 0.475 | 1.579 |
| Dehydrated cyclodextrin concentration (mmol/l) | | | | |
| 0.25 | 0.133 | 0.442 | 0.145 | 0.482 |
| 1.00 | 0.146 | 0.486 | 0.161 | 0.535 |
| 5.00 | 0.212 | 0.705 | 0.224 | 0.745 |
| 10.00 | 0.291 | 0.968 | 0.309 | 1.028 |
| 20.00 | 0.453 | 1.506 | 0.471 | 1.566 |

EXAMPLE 14

Temazepam/dehydrated β-CD 1:2 mol/mol physical mixtures compared with analogous drug β-CD system were tested according to Example 12.

The conditions of the tests were acetate buffer pH 5.5, 37° C., 80 rpm. The results are shown in Table 13.

TABLE 13

| Temazepam/β-cyclodextrin compositions 1:2 m/m | | |
|---|---|---|
| time (minutes) | hydrated β-CD (mcg/ml) | dehydrated β-CD (mcg/ml) |
| 5 | 5.3 | 10.7 |
| 10 | 9.9 | 18.4 |
| 15 | 13.9 | 22.3 |
| 20 | 17.2 | 25.1 |
| 30 | 21.6 | 28.6 |
| 60 | 28.9 | 33.6 |
| 90 | 32.2 | 35.4 |

EXAMPLE 15

Physical mixtures temazepam/β-CD 1:3 mol/mol were tested according to Examples 12 and 13, and the results are shown in

TABLE 14

| Temazepam/β-cyclodextrin compositions 1:3 m/m | | |
|---|---|---|
| time (minutes) | hydrated β-CD (mcg/ml) | dehydrated β-CD (mcg/ml) |
| 5 | 8.0 | 12.1 |
| 10 | 12.7 | 17.7 |
| 15 | 16.0 | 21.0 |
| 20 | 19.2 | 23.7 |
| 30 | 23.4 | 27.2 |
| 60 | 31.2 | 33.1 |
| 90 | 35.3 | 35.4 |

FORMULATION EXAMPLE

FCE 24304/dehydrated β-cyclodextrin (molar ratio 1:1 corresponding to 25 mg of active drug) mg 120

| Lactose | mg 60 |
|---|---|
| Crospovidone | mg 10 |
| Colloidal silicon dioxide | mg 0.5 |
| Glyderyl palmitostearate or magnesium stearate | mg 10 |

The FCE 24304/dehydrated β-CD physical mixture obtained according to Example 3 or co-ground composition according to Example 8 is admixed with the various indicated ingredients following conventional techniques.

We claim:

1. A solid pharmaceutical composition comprising at least an active drug substance and a cyclodextrin in dehydrated form, said cyclodextrin being in a molar ratio of from 0.5:1 to 10:1 over the drug and said solid pharmaceutical composition having a moisture content lower than 7% by weight.

2. A pharmaceutical composition according to claim 1 wherein said cyclodextrin is in a molar ratio of 4:1 to 1:1 over the drug.

3. A pharmaceutical composition according to claim 1 wherein the cyclodextrin is β-cyclodextrin.

4. A pharmaceutical composition according to claim 1 having a moisture content lower than 5%.

5. A process for preparing a pharmaceutical composition according to claim 1, which comprises mixing a powdered active drug substance and a powdered dehydrated cyclodextrin having a water content lower than 5%.

6. A process according to claim 5 wherein the cyclodextrin is dehydrated β-cyclodextrin.

7. A process according to claims 5 or 6, wherein said mixture is ground under such conditions that the moisture content of the mixture is lower than 7% by weight.

8. A process according to claim 5 or 6, wherein said active drug substance and said dehydrated cyclodextrin are mixed together under such conditions that the moisture content of the mixture is lower than 5% by weight.

9. A pharmaceutical formulation comprising a composition according to claim 1 and a pharmaceutically acceptable carrier or diluent.

* * * * *